United States Patent [19]

Miyake et al.

[11] Patent Number: 4,885,159

[45] Date of Patent: Dec. 5, 1989

[54] HIAR COSMETIC COMPOSITION

[75] Inventors: Miyuki Miyake, Narashino; Haruhiko Toda, Chiba; Minako Yasu, Tokyo, all of Japan

[73] Assignee: Lion Corporation, Tokyo, Japan

[21] Appl. No.: 149,337

[22] Filed: Jan. 28, 1988

[30] Foreign Application Priority Data

Feb. 2, 1987 [JP] Japan ................................. 62-22166

[51] Int. Cl.$^4$ ...................... A61K 7/06; A61K 9/14; A61K 9/50
[52] U.S. Cl. ...................................... 424/70; 424/78; 424/79; 424/81; 424/450; 252/DIG. 13
[58] Field of Search ..................... 424/79, 78, 450, 70, 424/81, 401, 487, 501, 486, 489, 490

[56] References Cited

U.S. PATENT DOCUMENTS 4,217,344  8/1980  Vanbergerghe et al. ........ 424/63 X
4,485,045  11/1984  Regen ............................. 424/450 X

OTHER PUBLICATIONS

Fendler, Janos H., "Polymerized Surfactant Vesicles: Novel Membrane Mimetic Systems", Science, 223 (4639), 1984, pp. 888-894.
J. Am. Chem. Soc. 106, 2446-2447 (1984).
J. Am. Chem. Soc. 106, 4279-4280 (1984).
J. Am. Chem. Soc. 108, 2321-2327 (1986).

*Primary Examiner*—Ellis P. Robinson
*Assistant Examiner*—Susan S. Ducker
*Attorney, Agent, or Firm*—Armstrong, Nikaido, Marmelstein, Kubovcik & Murray

[57] ABSTRACT

A hair cosmetic composition comprising a polymer vesicle obtained from the polymerization of a surfactant monomer vesicle haing quaternary ammonium as a cation moiety and a polymerizable anion as a counter ion.

7 Claims, No Drawings

HIAR COSMETIC COMPOSITION

BACKGROUND OF THE INVENTION

1. Field of the Invention

The present invention relates to a hair cosmetic composition capable of moisturizing hair and of protecting the hair from damage. More specifically, it relates to a hair cosmetic composition having an improved hair rinse effect and an improved protection of the surface of the hair, which are obtained by improving the adsorptivity of a hair cosmetic component.

2. Description of the Related Art

Conventional hair cosmetic compositions generally contain quaternary ammonium salts such as alkyl trimethyl ammonium chlorides and dialkyl dimethyl ammonium chloride as a component for providing flexibility and glossiness to the hair, and for preventing an electrical charge in hair, and fats and oil represented by higher alcohols can be generally formulated to strengthen the above-mentioned effects.

Conventional hair cosmetic compositions, however, do not provide completely satisfactory effects, since the adsorptivity of the quaternary ammonium salts is poor. Therefore, because the hair is now more susceptible to damage due to the growing popularity of, for example, permanent waving, hair coloring, and drying, a problem arises in that the above-mentioned conventional hair cosmetic compositions do little to prevent such damage to the hair.

In view of the above, various attempts have been made to improve the hair damage prevention effects by using, as a protective agent for the hair surface, various polymers such as cellulose type, keratin type, and vinyl type polymers in hair cosmetic compositions, but these proposed compositions still do not provide satisfactory protection against damage to the hair. This is believed to be because the polymer cannot be supplied as a fine particle dispersion, and thus the polymer particles cannot be uniformly adsorbed on the surface of the hair because the polymer acts as a flocculating agent or thickening agent.

For the above-mentioned reasons, the conventional hair cosmetic compositions could be improved by formulating therein a moisturizing agent such as polysiloxane or sodium pyrrolidone carboxylate, in addition to the above-mentioned components, for obtaining an improved finish, but a hair cosmetic composition capable of satisfactorily obtaining the required damage prevention and moisturizing effects, especially under severe conditions such as the use of a hair dryer, has not been provided.

SUMMARY OF THE INVENTION

Accordingly, the objects of the present invention are to eliminate the above-mentioned disadvantages of the prior art and to provide a hair cosmetic composition having excellent moisturizing and damage prevention effects by improving the adsorptivity of the hair cosmetic components and thus improve the hair rinsing and hair surface protection effects.

Other objects and advantages of the present invention will be apparent from the following description.

In accordance with the present invention, there is provided a hair cosmetic composition comprising a polymer vesicle obtained from the polymerization of a surfactant monomer vesicle having quaternary ammonium as a cation moiety and a polymerizable anion as a counter ion.

DESCRIPTION OF THE PREFERRED EMBODIMENTS

As mentioned above, according to the present invention, the following technique has been adopted for uniformly and effectively adsorbing quaternary ammonium salts, which are used as a main component in conventional hair cosmetic compositions, and polymers, which are used as a protective agent in conventional hair cosmetic compositions, on the surface of the hair to obtain the desired characteristics. That is, according to the present invention, fine vesicles of quaternary ammonium type surfactants having a polymerizable anion introduced thereto as a counter ion are prepared and the counter ion is allowed to polymerize on the surface of the vesicle, whereby fine polymer vesicles having quaternary ammonium salts in the structure thereof are formed. The excellent hair surface protection and moisturizing effects of the polymer vesicles are utilized in the present invention.

The surfactants forming the polymer vesicles according to the present invention include quaternary ammonium salts having the following general formula (I), in which two long chain type cationic portions and a polymerizable anion counter ion portion are contained.

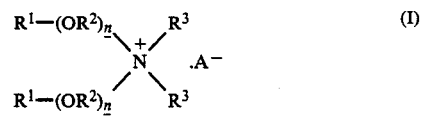

(I)

wherein $R^1$ represents a linear or branched alkyl or alkylaryl having 8 to 32 carbon atoms, $R^2$ represents alkyl having 2 to 3 carbon atoms, n is an integer of 0 to 5, $R^3$ represents an alkyl having 1 to 4 carbon atoms or $-(OR_2)_nH$, and a counter ion $A^-$ represents an organic acid type anion having a polymerizable group.

The counter ion parts $A^-$ in the general formula (I) usable in the present invention are polymerizable organic acid type ions. Examples of such organic acid type ions are carboxylic acid type anions such as acrylic acid ion and methacrylic acid ion and sulfuric acid type anions such as vinyl sulfonic acid ion, styrene sulfonic acid ion, and 2-acrylamide-2-methylpropane sulfonic acid ion. Of these anions, preferably carboxylic acid type ions such as acrylic and methacrylic ions, more preferably methacrylic ions, are used.

The quaternary ammonium salt monomers having the formula (I) capable of forming the polymer vesicles can be synthesized by, for example, ion-exchanging the halogen ion of halogenated quaternary ammonium salt with an organic acid type anion having a polymerizable group by an ion exchange resin (see J. Am. Chem. Soc., 106, 2446–2447 (1984) and J. Am. Chem. Soc., 108, 2321–2327 (1986)). Alternately, a halogenated alkali metal salt may be removed by a desalting method from an alkali metal salt of an organic acid and a halogenated quaternary ammonium salt, whereby the desired quaternary ammonium salt monomer (I) may be synthesized.

According to the present invention, the desired polymer vesicle is obtained by preparing the quaternary ammonium salt type surfactant having the formula (I) in the form of a vesicle, followed by the polymerization thereof. The preparation of the vesicle dispersion is carried out by an ultrasonic treatment. The temperature during the treatment is preferably 50° C. or higher and the concentration of the surfactant during the treatment is preferably 0.1% to 5% by weight.

The polymerization for preparing the polymer vesicle according to the present invention may be carried out by either conventional photopolymerization methods (see J. Am. Chem. Soc., 106, 2446-2447 (1984), J. Am. Chem. Soc., 108, 2321-2327 (1986)), or by thermal polymerization methods.

In the case of photopolymerization, as the light source for irradiating light, a method using a low-pressure mercury vapor lamp having a wavelength of 254 mm, a method using a high-pressure mercury vapor lamp having a wavelength of 360 mm, and a method using a high-pressure mercury vapor lamp in the presence of a photosensitizer may be used. Furthermore, both an internal irradiation and an outside irradiation method can be used as the irradiation method.

In the case of thermal polymerization, a radical initator is used, and examples of such radical initators are water-soluble initiators such as persulfates, 2-carbamoylazo-isobutyronitrile, 2,2'-azobis(N,N'-dimethyleneisobutylamidine) dihydrochloride, 2,2'-azobis(2-amidinopropane) dihydrochloride, and 4,4'-azobis(4-cyanopentanoic amide), and oil-soluble initiators such as 2,2'-azobis(4-methoxy-2,4-dimethylvalenonitrile), 2,2'-azobis(2,4-dimethylvalenonitrile), (1-phenylethyl) azodiphenylmethane, 2,2'-azobisisobutyronitrile, dimethyl-2,2'-azobisbutyrate, 2,2'-azobis(2methylbutyronitrile), and 1,1'-azobis(1-cyclohexane carbonitrile). The polymerization temperature is preferably 60 to 90° C., and a high polymerization conversion can be obtained at a polymerization time of, preferably, 5 to 6 hours.

The polymer vesicles obtained as mentioned above preferably have a particle size of 10 to 1000 nm, more preferably 10 to 200 nm. The degree of the polymerization in the vesicles is preferably 2 to 600, more preferably 2 to 400.

It is considered that the hair cosmetic compositions comprising the polymer vesicles exhibit superior characteristics to the conventional hair cosmetic compositions for the following reasons.

According to the present invention, since the counter ion portion is polymerized within bilayer membrane vesicles, the vesicles are formed in a fine and uniform bilayer membrane-polymer composite structure. Furthermore, the polymer chains formed by polymerization provide hydrophobic surfaces, which are not found on vesicles of conventional quaternary ammonium salts and vesicles before the polymerization according to the present invention, and therefore, the affinity to hydrophobic surfaces such as hair surfaces is improved. In addition, since the fine shapes or configuration are retained after polymerization, the present vesicles can be effectively adsorbed on the surface of the hair and, as a result, the hair is protected by widely covering the surface with the bilayer membrane-polymer composite.

On the other hand, although composite materials can be formed by mixing conventional cationic ammonium salts and anionic polymer substances, larger particles, in which the composites are only partly formed due to the flocculating action of the anionic polymer, exist in the thus-formed composites. Therefore, the adsorption to the hair becomes nonuniform, and the protection effect is lowered.

When the adsorption to the surface of hair of the polymer vesicles according to the present invention and for a conventional mixture of quaternary ammonium salts and anionic polymers were compared under a scanning type electron microscope, the following results were obtained. Namely, the surface adsorbed with the polymer vesicles according to the present invention was uniformly covered by the fine particles and the design or pattern of the cuticles became unclear. Contrary to this, the surface adsorbed with the conventional mixture of quaternary ammonium salt and anionic polymer contained a portion adsorbed with the agglomerated large particles, and non-adsorbed portions were observed.

In view of the above results, it can be understood that, since the polymer vesicles according to the present invention have an effective adsorptivity and uniform composite structure, the protection of the surfaces of the hair is greater than that of conventional hair cosmetic compositions, and the desired excellent moisturizing and hair damage prevention effects can be obtained.

Although there are no critical limitations to the amount of the polymer vesicle in the hair cosmetic composition, the preferable amount is 0.1% to 10% by weight, more preferably 0.5% to 3% by weight, based on the total amount of the hair cosmetic composition.

The hair cosmetic composition of the present invention can be prepared and applied as the first agent in a permanent wave treatment, shampoo, hair liquid, hair tonic, foamy hair-care material, and the like. The hair cosmetic composition of the present invention can formulate optional conventional components in addition to the above-mentioned polymer vesicle, depending upon the kind of cosmetic composition desired. Examples of such components are oil components such as silicon derivatives, hydrocarbons, ester oils, higher fatty acids, high alcohols, lanolin derivatives; nonionic surfactants, anionic surfactants, amphoteric surfactants, vitamin A, $B_6$, $B_{12}$, C, D, E, H and derivatives thereof, protein hydrolysates, amino acids, animal and vegetable extracts, nonionic resins such as polyvinylpyrrolidone and derivatives thereof; anionic resins such as methylvinyl ether-butyl maleate copolymer; amphoteric resins such as acrylic acid-methacrylate copolymers; UV-ray absorbers such as oxybenzoin derivatives, cinnamic acid ester derivatives; coolness imparting agents such as l-menthol, peppermint oil; stimulation imparting agents such as benzyl nicotinate, Guinea pepper tincture; sterilizers such as gluconic acid chlorohexidine, isopropylmethylphenol; preservatives such as paraben; perfumes, dyes, and deterioration preventives.

The present hair cosmetic composition can be readily prepared in any conventional manner. For example, the above-mentioned essential and optional components may be mixed together in an aqueous medium.

As explained above, according to the present invention, the hair cosmetic composition comprising the polymer vesicles having the uniform bilayer membrane-polymer composite structure and exhibiting excellent moisturing and damage prevention effects due to the superior hair surface protection effect of the polymer obtained from their excellent adsorptivity, can be provided.

EXAMPLES

The present invention will now be further described in more detail by referring to, but is by no means limited to, Examples and Comparative Examples, in which all percentages are % by weight unless otherwise specified.

Example 1

As a starting material, distearyl dimethyl ammonium chloride (i.e., Arquard 2HT-75 commercially available from LACO Co.) was used after recrystallization from acetone. This distearyl dimethyl ammonium chloride actually contained 70% of a linear alkyl group having 18 carbon atoms and 30% of a linear alkyl group having 16 carbon atoms.

An anion exchange resin (i.e., Amberlist A-27 commercially available from Organo K.K.) was packed into a column and a methanol solution of methacrylic acid (commercially available from Junsei Chemical K.K.) was passed through the column to obtain a methacrylate type ion exchange resin. The above-mentioned distearyl dimethyl ammonium chloride in a methanol solution was then passed through the column to exchange the counter ions thereof. The solvent, i.e., methanol, was concentrated followed by recrystallization from acetone, and the desired polymerizable quaternary ammonium surfactant 2HT methacrylate having a methacrylate moiety introduced therein at the counter ion part was obtained in the form of a white crystal.

A 5 g amount of the 2HT methacrylate obtained above and 250 g of water were placed in an Erlenmeyer flask, and the flask was sealed and then subjected to an ultrasonic treatment for 2 to 4 hours, while heating at a temperature of 70° C. to 80° C., by using a water bath type ultrasonic treatment apparatus (Model 521 manufactured by Bransonic Co.), to obtain the desired vesicle dispersion. The bilayer membrane structure of vesicle of this dispersion was confirmed by a transmission type electron miscoscope (Hitachi H-600) according to a freeze fracture type replica method.

A 250 ml amount of the vesicle dispersion prepared above was placed in a reaction vessel, and polymerization was carried out by using a low pressure mercury vapor lamp (Model UVL-32LB available from Rikou Kagaku Sangyo Co., 32 W, wavelength 254 nm) in an internal irradiation method. When the disappearance of the olefin proton peak and methacrylate methyl proton peak was monitored by NMR, it was confirmed that the polymerization reaction was completed in 6 hours. The resultant polymer vesicle dispersion thus obtained contained vesicles having a particle size of 67 nm, as measured by a submicron sizer (Model B-90 manufactured by Brookhaven Co.) and having a main distribution of a degree of polymerization of 4 to 30.

Example 2

The recrystallized distearyl dimethyl ammonium chloride used in Example 1 and potassium methacrylate (available from Wako Pure Chemical Ind. Ltd.) were stirred, while heating, in methanol at a temperature of 50° C. for 5 hours and, after the excess potassium methacrylate was filtered off, the methanol was concentrated and dried to solidify the resultant mixture. The solidified product was dissolved in methylene dichloride and, after the undissolved potassium chloride was filtered off, the methylene dichloride salt was distilled off. The resultant white solid was recrystallized from acetone to obtain the desired 2HT methacrylate having methacrylate introduced therein, at the counter ion part, in the form of the white solid.

A 5 g amount of the 2HT methacrylate obtained above and 250 g of water were placed in an Erlenmeyer flask and the ultrasonic treatment and photopolymerization were carried out in the same manner as in Example 1. The vesicles of the resultant polymer vesicle dispersion had a particle size of 74 nm, as measured by the submicron sizer used in Example 1, and a degree of polymerization of 4 to 26.

To evaluate the hair cosmetic compositions of the present invention containing the polymer vesicles obtained in Examples 1 and 2, the following hair cosmetic compositions according to Comparative Examples 1 to 3 were prepared. The comparative samples were those obtained by a conventional technique or having a formulation such that a portion of the present formulation was omitted.

COMPARATIVE EXAMPLE

A 5 g amount of the distearyl dimethyl ammonium chloride used in Example 1 and 250 g of water were placed in an Erlenmeyer flask, the mixture was subjected to the ultrasonic treatment as in Example 1, and a comparative vesicle dispersion was obtained.

COMPARATIVE EXAMPLE 2

Potassium polymethacrylate was obtained by thermally polymerizing a 5% aqueous solution of potassium methacrylate used in Example 2, in the presence of an ammonium persulfate initiator.

The resultant aqueous potassium polymethacrylate solution was added to the vesicle dispersion of Comparative Example 1 in an amount such that the methacrylic acid unit became an equal mole to the 2HT molecule in vesicle. Thereafter, the ultrasonic treatment of Example 1 was carried out at a temperature of 50° C. for 30 minutes to obtain the comparative mixture dispersion.

COMPARATIVE EXAMPLE 3

A 5 g amount of the 2HT methacrylate obtained in Example 1 and 250 g of water were placed in an Erlenmeyer flask, the ultrasonic treatment of Example 1 was applied to the mixture, and a comparative vesicle dispersion was obtained.

The adsorptivity the water retention percentage of the vesicle dispersions of Examples 1 and 2 and Comparative Examples 1, 2, and 3 were evaluated with regard to the use of a dryer, the absence of harshness of the hair tips, the hair combing load, the hair luster, and the abrasion resistance, as follows. The results are shown in Table 1.

Evaluation Method

1. Adsorptivity

A 3 g bundle of hair was thoroughly washed with a 1% aqueous sodium α–olefin sulfonate solution and, after rinsing with running water, the hair bundle was dipped in 50 ml of a 0.2% aqueous vesicle dispersion and allowed to stand at a temperature of 40° C. for 30 minutes. Accordingly, the vesicles were adsorbed on the hair. The hair bundle was then removed from the dispersion and adhered water removed by squeezing. The amount of vesicle remaining in the dispersion was measured and the amount of vesicles adsorbed to the hair was calculated by subtracting the amount remaining from the original amount of vesicles.

2. Water Retention Percentage

After a 10 g bundle of hair having a length of 30 cm was bleached, the hair bundle was thoroughly washed with a 1% aqueous sodium α-olefin sulfonate solution, followed by rinsing with running water and drying with a towel. To the hair bundle, 2 ml of a 1% aqueous vesicle dispersion was uniformly coated, followed by rinsing with water and drying with a towel.

A hair dryer was applied to the obtained hair bundle for 10 minutes from a point 10 cm away from the hair bundle and, thereafter, the weight ($W_1$) of the hair bundle was measured.

The weight ($W_2$) of the hair bundle was also measured after vacuum drying at a temperature of 90° C. The water retention percentage was determined from the following equation.

$$\text{Water retention (\%)} = \frac{W_1 - W_2}{W_2} \times 100$$

$W_1$: Weight of hair bundle after drying with a dryer
$W_2$: Weight of hair bundle after 90° C. vacuum drying

3. Harshness of Hair Tip

The hair bundle was subjected to the abovementioned treatment used in the case of the water retention measurement, except that the bleach treatment was not carried out. Thereafter the hair bundle was combed 7 times. This treatment was repeated 6 times and the absence of harshness of the hair tips was organoleptically evaluated by a paired-comparison method. The evaluation was carried out according to the following scores. That is, in a paired-comparison method, an α value obtained when only distearyl dimethyl ammonium chloride (2HT) was formulated, was designated as a score "3" and an α value of untreated hair was designated as a score "1". From these standards, the score of each sample was determined based on the obtained α value.

4. Flyaway

The hair bundle used in the evaluation 3 was combed and the width of the bottom of the spread hair bundle was measured.

5. Combing Load

The hair bundle used in the above-mentioned evaluation of flyaway was set in a strain gauge and, when a comb fixed in a tensilon meter was moved at a rate of 4 cm/min, the load applied to the hair bundle was measured.

6. Hair Luster

A hair bundle composed of 50 hairs having a length of 25 cm was treated with a shampoo and, after towel drying, the hair bundle was dipped in 5 ml of a 1% aqueous vesicle dispersion at a temperature of 40° C. for 5 minutes, followed by rinsing with water and the hair bundle was dried at a temperature of 25° C. under a relative humidity (R.H.) of 65%.

The static abrasion coefficient of the hair bundle was determined when the hair bundle was rotated at 2.5 rpm, and thus the hair luster was evaluated.

7. Abrasion Resistance

The hair bundle was treated in the same manner as in the evaluation of the hair luster. The abrasion coefficient was measured when the hair bundle was rotated at 50 rpm, and thus the abrasion resistance was evaluated.

TABLE 1

|  | Adsorptivity | Water retention | Absence of harshness of hair tip | Hair away | Hair combing load | Hair luster | Abrasion resistance |
|---|---|---|---|---|---|---|---|
| Evaluation Item | 40° C., 30 min. Standing 0.2%, 50 ml | Bleach treated hair bundle | Characteristics after 6 times rinse treatment of normal hair | | | Abrasion coefficient | direction. Pulley 50 rpm. |
| | | | | | | direction abrasion | |
| Conditions | 3 g hair bundle | Dryer drying 10 min. | | | | Pulley 2.5 rpm | Abrasion coefficient after 5 min. |
| Example 1 | 98% | 12% | score 5 | 15 cm | 494 g | 0.10 | 0.27 |
| Example 2 | 97% | 11.9% | score 5 | 15 cm | 485 g | 0.11 | 0.30 |
| Comparative Example 1 | 21% | 8.2% | score 3 | 20 cm | 603 g | 0.22 | 0.73 |
| Comparative Example 2 | — | 10% | score 4 | 18 cm | 521 g | 0.13 | 0.57 |
| Comparative Example 3 | 36% | 10.1% | score 3 | 22 cm | 545 g | 0.16 | 0.78 |

As is clear from the results shown in Table 1, the absorptivity to the hair of the polymer vesicle dispersions of Examples 1 and 2 according to the present invention was much higher than that of Comparative Examples 1 and 3; proving the superiority of absorptivity of the present polymer vesicle.

Further, when the hair bundle was rinsed with each dispersion, followed by drying with a hair dryer for 10 minutes, the water retention percentages of the hair bundles treated with the polymer vesicles of Examples 1 and 2 were highest. Also, the polymer vesicles of Examples 1 and 2 according to the present invention exhibited the greatest effects for suppressing harshness of the hair tips and flyaway due to damage to and a decrease in water content of the hair when the hair bundle was subjected to a rinse treatment, hair dryer drying, and repeated brushing. Actually, the load applied to hair treated with the polymer vesicles of Examples 1 and 2 according to the present invention, when combing, is lowest and the damage of hair and harshness of the hair tips.

Moreover, the abrasion coefficient of the surface of hair treated with each dispersion was lowest when treated with the polymer vesicles of EXAMPLES 1 and 2 according to the present invention and, therefore, the hair luster and the abrasion resistance were excellent and the protection of the surface of the hair was high.

As mentioned above, when the dispersions of Examples 1 and 2 were used, it was confirmed that excellent moisturizing effects and damage prevention effects can be clearly obtained in all of the evaluation methods.

EXAMPLE 3

A vesicle dispersion was prepared from 4 g of the 2HT methacrylate obtained by a desalting method in Example 2 and 400 g of water, by applying the ultrasonic treatment of Example 1.

The resultant vesicle dispersion was placed in a reaction vessel and the photopolymerization was carried out for 13 hours according to an internal irradiation method using a high pressure mercury vapor lamp (Model UVL-400HA manufactured by Rikou Sangyo K.K., 400 W, wavelength 360 nm). In the photopolymerization, 50 mM of 2,2'-azobisisobutyronitrile was added as a photosensitizer.

The resultant vesicles had a particle size of 78 nm, as measured by the submicron sizer used in Example 1, and a main distribution range of a degree of polymerization of 2 to 80.

EXAMPLE 4

A vesicle dispersion was prepared from 4 g of the 2HT methacrylate obtained by the desalting method of Example 2 and 200 g of water, which were placed in an Erlenmeyer flask followed by applying the ultrasonic treatment of Example 1. The resultant dispersion was transferred to a 4-necked glass separable flask and 0.6 g of 2,2'-azobis(2-amidino propane) dihydrochloride was added separately three times as a radical initiator. The thermal polymerization was then carried out at a temperature of 60° C. for 6 hours in an $N_2$ stream, while stirring.

The polymer vesicles thus obtained had a particle size of 84 nm, as measured by the submicron sizer used in Example 1, and a degree of polymerization of 2 to 150.

Example 5

A vesicle dispersion was prepared from 2 g of the 2HT methacrylate obtained by the desalting method of Example 2 and 200 g of water, which were placed in an Erlenmeyer flask followed by applying the ultrasonic treatment of Example 1. The resultant dispersion was transferred to the same reaction flask as used in Example 4 and 1 g of 2,2'-azobisisobutyronitrile was added separately two times as a radical initiator and the thermal polymerization was carried out at a temperature of 90° C. for 5 hours in an $N_2$ stream.

The resultant polymer vesicle suspension had a particle size of 67 nm, as measured by the submicron sizer used in Example 1, and a degree of polymerization of 2 to 20.

The following Comparative Examples 4 and 5 are comparative examples of the above-mentioned Examples 3 to 5.

COMPARATIVE EXAMPLE 4

A 5 g amount of the same 2HT methacrylate as used in Example 2 and 250 ml of water were placed in an Erlenmeyer flask, followed by heating at a temperature of 80° C., while stirring, to prepare the vesicle dispersion. The vesicle dispersion was photopolymerized in the same manner as in Example 1, and the resultant polmmer vesicle dispersion was viscous. The particle size, as measured by the submicron sizer, was 3000 nm and the degree of polymerization was 2 to 120.

COMPARATIVE EXAMPLE 5

The vesicle dispersion obtained in the same manner as in Comparative Example 4 was thermally polymerized as in Example 4, and the resultant polymer vesicle dispersion was in the form of a gel. The particle size was 5000 nm, as measured by the submicron sizer, and the degree of polymerization was 2 to 700.

When the polymer vesicles of Comparative Examples 4 and 5 and Examples 3 to 5 were used for treating hair, and the treated hair was compared, the hair treated with the resides of Examples 3 to 5 exhibited a greater moisturizing effect and damage prevention effects. From these results, the optimum ranges of the particle size and degree of polymerization may be obtained.

The following Examples illustrate polymer vesicles derived from materials other than 2HT methacrylate.

EXAMPLE 6

As a starting quaternary ammonium salt, didodecyl dimethyl ammonium bromide (commercially available from Sougo Yakko K.K.) having two linear $C_{12}$ alkyl chains was used and didodecyl dimethyl ammonium methacrylate having methacrylate introduced at the counter ion part was obtained by the same desalting method as used in Example 2. A 1 g amount of the didodecyl dimethyl ammonium methacrylate and 100 g of water were placed in an Erlenmeyer flask and a vesicle dispersion was prepared in the same manner as in Example 1. The photopolymerization of the vesicle dispersion was also carried out in the same manner as in Example 1.

The resultant vesicle had a particle size of 21 nm, as measured by the submicron sizer, and a degree of polymerization of 2 to 15.

EXAMPLE 7

As a starting quaternary ammonium salt, ditetradecyl dimethyl ammonium bromide having two linear $C_{14}$ alkyl chains (commercially available from Sougo Yakko K.K.) was used, and ditetradecyl dimethyl ammonium methacrylate having methacrylate introduced into the counter ion was obtained by the same desalting method as used in Example 2. Thereafter, a polymer vesicle comprising ditetradecyl dimethyl ammonium methacrylate was prepared in the same manner as in Example 6.

The resultant polymer vesicles had a particle size of 34 nm, as measured by the submicron sizer, and a degree of polymerization of 2 to 15.

EXAMPLE 8

As a starting quaternary ammonium salt, dihexadecyl dimethyl ammonium bromide having two linear $C_{16}$ alkyl groups (commercially available from Sougo Yakko K.K.) was used and ditetradecyl dimethyl ammonium methacrylate having methacrylate introduced into the counter ion part thereof was obtained by the same desalting method as used in Example 2. Thereafter, polymer vesicles comprising dihexadecyl dimethyl ammonium methacrylate were prepared in the same manner as in Example 6. The polymer vehicles had a particle size of 46 nm, as measured by the submicron sizer, and a degree of polymerization of 2 to 15.

EXAMPLE 9

As a starting quaternary ammonium salt, dioctadecyl dimethyl ammonium chloride having two linear $C_{18}$ alkyl chains (commercially available from Tokyo Kasei Kogyo K.K.) was used and dioctadecyl dimethyl ammonium methacrylate having methacrylate introduced into the counter ion part by the same desalting method as used in Example 2. Thereafter, polymer vesicles comprising dioctadecyl dimethyl ammonium methacrylate were prepared in the same manner as in Example 6. The polymer vesicles had a particle size of 46 nm, as measured by the submicron sizer, and a degree of polymerization of 2 to 15.

EXAMPLE 10

A methanol solution of acrylic acid was passed through a column packed with the same ion exchange resin as used in Example 1, to obtain acrylate type ion exchange resin. Then, a methanol solution of the same distearyl dimethyl ammonium chloride as used in Example 1 was passed through the column. According to the same procedure as used in Example 1, polymerizable quaternary ammonium surfactant 2HT acrylate having acrylate introduced into the counter ion part was obtained. A 5 g amount of the 2HT acrylate and 250 g of water were placed in an Erlenmeyer flask and the ultrasonic treatment and the photopolymerization was carried out in the same manner as in Example 1. As a result, the desired polymer vesicles having a particle size of 40 nm, as measured by the submicron sizer, and a degree of polymerization of 2 to 10 were obtained.

Example 11

2-Acrylamide-2'-methylpropane sulfonic acid ("AMPS" commercially available from Tokoyo Kassi Kogyo K.K.) was passed through a column packed with the same ion exchange resin to obtain an AMPS type ion exchange resin. The water solvent was replaced by methanol, and thereafter, a methanol solution of the same distearyl dimethyl ammonium chloride as used in Example 1 was passed through the column to obtain a polymerizable quaternary ammonium surfactant 2HT AMPS having AMPS introduced into the counter ion part.

A 5 g amount of the 2HT AMPS obtained above and 250 g of water were placed in an Erlenmeyer flask and the same ultrasonic treatment and photopolymerization as used in Example 1 were carried out. Accordingly, the desired polymer vesicle dispersion having a particle size of 82 nm, as measured by the submicron sizer, and a degree of polymerization of 2 to 110 was obtained.

The hair cosmetic compositions containing the polymer vesicles obtained in Examples 6 to 11 exhibited excellent moisturizing and damage prevention effects.

The Formulation Examples in which the polymer vesicles of Example 2 as well as a higher alcohol, a nonionic surfactant, and an oil, etc., were formulated will now be explained.

FORMULATION EXAMPLE 1

| Ingredient | % |
| --- | --- |
| Polymer vesicle dispersion | 60 |
| Cetostearyl alcohol | 3 |
| Polyethyleneoxide (5 mol) stearyl ether | 2 |
| Propylene glycol | 5 |
| Water | balance |

FORMULATION EXAMPLE 2

| Ingredient | % |
| --- | --- |
| Polymer vesicle dispersion | 45 |
| Cetostearyl alcohol | 5 |
| Glycerol monostearate | 0.5 |
| Sorbitan sesquioleate | 0.5 |
| Glycerol | 10 |
| Water | balance |

FORMULATION EXAMPLE 3

| Ingredient | % |
| --- | --- |
| Polymer vesicle dispersion | 75 |
| Cetostearyl alcohol | 7 |
| Lauric monoethanol amide | 1 |
| Propylene glycol | 5 |
| Vaselin | 2 |
| Water | balance |

The hair cosmetic compositions obtained in Formulation Examples 1 to 3 according to the present invention all had excellent moisturizing and damage prevention effects. Note, the kinds and formulation amounts of each component are by no means limited to the above-mentioned Examples.

I claim:

1. A hair cosmetic composition comprising a polymer vesicle obtained by the polymerization of a surfactant monomer vesicle having the formula (I):

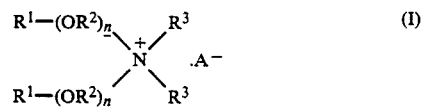

wherein $R_1$ represents a linear or branched alkyl or alkylaryl having 8 to 32 carbon atoms, $R^2$ represents alkyl having 2 to 3 carbon atoms, n is an integer of 0 to 5, $R_3$ represents an alkyl having 1 to 4 carbon atoms $-(OR_2)_nH$, and a counter ion A represents an organic acid type anion having a polymerizable group.

2. A hair cosmetic composition as claimed in claim 1, wherein the particle size of the polymer vesicle is 10 to 1000 mm.

3. A hair cosmetic composition as claimed in claim 1, wherein the amount of the polymer vesicle formulated is 0.1% to 10% by weight based on the total amount of the composition.

4. A hair cosmetic composition as claimed in claim 1, wherein the degree of polymerization of the polymer vesicle is 2 to 600.

5. A hair cosmetic composition as claimed in claim 2, wherein the amount of polymer vesicle is about 0.1 to 10% by weight, based on the total composition weight.

6. A hair cosmetic composition as claimed in claim 2, wherein the polymer vesicle degree of polymerization is about 2 to 600.

7. A hair cosmetic composition as claimed in claim 3, wherein the polymer vesicle degree of polymerization is about 2 to 600.

* * * * *